United States Patent [19]

Jirousek et al.

[11] Patent Number: 6,093,709
[45] Date of Patent: Jul. 25, 2000

[54] THERAPEUTIC TREATMENT FOR SEXUAL DYSFUNCTIONS

[75] Inventors: Michael R. Jirousek, Hamberg, Germany; Douglas Kirk Ways; Lawrence E. Stramm, both of Indianapolis, Ind.

[73] Assignee: Eli Lilly and Company, Indianapolis, Ind.

[21] Appl. No.: 08/915,303

[22] Filed: Aug. 19, 1997

Related U.S. Application Data

[60] Provisional application No. 60/023,425, Aug. 22, 1996.

[51] Int. Cl.$^7$ .................................................. A61K 31/395
[52] U.S. Cl. ............................................ 514/183; 514/185
[58] Field of Search ....................................... 514/183, 185

[56] References Cited

U.S. PATENT DOCUMENTS

| | | |
|---|---|---|
| 5,057,614 | 10/1991 | Davie et al. . |
| 5,481,003 | 1/1996 | Gillig et al. . |
| 5,491,242 | 2/1996 | Gillig et al. . |
| 5,545,636 | 8/1996 | Heath et al. . |
| 5,552,396 | 9/1996 | Heath et al. ............................. 514/183 |
| 5,621,098 | 4/1997 | Heath et al. . |
| 5,658,936 | 8/1997 | Kifor et al. ............................. 514/381 |

OTHER PUBLICATIONS

H. Bundgaard, *Design of Prodrugs*, (1985).
Frank E, et al., 1978. N Engl J Med 299:111.
Goldstein M and Teng N. 1991. Clin Geriatr Med 7:41.
Park K et al., 1997. Int J Impot Res 9:27.
Sadeghi–Nejad H et al., 1996. J Urol 155:677A.
Slob A et al., 1990. J Sex Martial Ther 16:59.
Thirlaway K et al., 1996. Quality of Life Res 5:81.
International Search Report mailed Jan. 14, 1998.
Proceedings of the American Urological Association, vol. 155, May 1996, Supp. 677A, Abst Nos. 163–66.
Cheng, H.C., MDL 27,032, 1991.

*Primary Examiner*—James H. Reamer
*Attorney, Agent, or Firm*—Paul R. Darkes

[57] ABSTRACT

A method for treating sexual dysfunctions is disclosed, particularly using the isozyme selective PKC inhibitor, (S)-3,4-[N,N'-1,1'-((2"-ethoxy)-3'"(O)-4'"-(N,N-dimethylamino)-butane)-bis-(3,3'-indoly1)]-1(H)-pyrrole-2, 5-dione, particularly its hydrochloride, or mesylate salt.

18 Claims, No Drawings

THERAPEUTIC TREATMENT FOR SEXUAL DYSFUNCTIONS

This application claims the priority benefits from the U.S. Provisional application Serial No. 60/023,425, filed Aug. 22, 1996.

BACKGROUND OF THE INVENTION

1. Field of the Invention

The present invention is broadly directed to a method for inducing endothelium dependent vasodilation, smooth muscle relaxation, especially such events associated with sexual functions, e.g., penile erection, clitoral engorgement and erection. The present invention is particularly directed to the use of a particular class of isozyme selective Protein Kinase C (PKC) inhibitors for treating sexual dysfunctions, e.g., impotence in diabetic men and arousal and orgasm disorders in women.

2. Description of Related Art

The prevalence of impotence in diabetic men has been reported to be as high as 50 percent. The neurologic and vascular complications of diabetes are presumed to be responsible for the associated erectile dysfunction. Studies in animal models of diabetes. as well as in humans, have uncovered pathologic changes in penile arteries, morphologic alterations of autonomic nerves, and a depletion of neurotransmitters within the corpus cavernosum.

Vasodilation and relaxation of the smooth muscle of the corpus cavernosum lead to penile erection. Dilation of the arterioles that perfuse the lacunar spaces and relaxation of the corporal smooth muscle that surrounds these spaces result in the engorgement of the corporal bodies with blood. The expansion of the lacunar spaces against the tunica albuginea, which encloses the corpora, causes the compression of subtunical venules, restricts blood outflow, and leads to an increase in intracavernosal pressure to a value approximating the mean systemic arterial blood pressure. Thus, it is thought that the impairment of the mechanisms of vasodilation and relaxation of corporal smooth muscle may result in impotence.

The relaxation of penile corporal smooth muscle is controlled locally by nerves that release cholinergic and nonadrenergic, nonocholinergic neurotransmitters; as well as by the vascular endothelium, which lines the lacunar spaces and releases endothelium-derived relaxing factor. Sympathetic nerves cause the contraction of penile corporal smooth muscle by alpha-adrenergic mechanisms and mediate the detumescence of the erect penis.

Medical therapy with androgens offers little more than placebo benefit except in hypogonadal men. Surgical therapy may be useful in the treatment of decreased potency related to aortic obstruction; however, potency can be lost rather than improved after aortic operation if the autonomic nerve supply to the penis is damaged inadvertently. This complication can be minimized if an endarterectomy is done or, in a grafting procedure, if the reconstruction of the distal end is performed above the origin of the external iliac arteries. Early surgical relief of priapism by shunting procedures, such as corpora spongiosum shunting might prevent subsequent impotence.

Another surgical therapy for improvement of potency in refractory patients such as individuals with diabetic neuropathy is the implantation of a penile prosthesis, namely the insertion within the corpora of a small, blunt silastic rod. However, full erection is not produced and the device only prevents buckling during intercourse. Furthermore, the complication rate is high in some series. Alternatively, an inflatable prosthetic device has been devised for implantation on either side of the corpora. A connecting reservoir of material then is placed in the perivesicular space and pumps are located in the scrotum. By means of these pumps the penis can be made to become nearly fully erect at the appropriate time and to relax after intercourse.

As one can appreciate, the presently available treatment for impotence, especially impotence in diabetic men, is not fully satisfactory. There remains a need in the art to develop improved ways to treat impotence, especially impotence in diabetic men.

Sexual functions in females can be divided into several broad areas: desire, arousal, and orgasm. Studies have indicated that up to 63% of women exhibit dysfunctions in either arousal or orgasmic stages of sexual activities (Frank E, et al., 1978. N Engl J Med 299: 111). Sexual disorders such as dyspareunia and vaginismus, reduce the arousal phase of female sexual functioning. Impaired clitoral responsiveness can lead to orgasmic disorders. The prevalence of female sexual dysfunction increases with age (Goldstein M and Teng N. 1991. Clin Geriatr Med 7:41; Thirlaway K et al., 1996. Quality of Life Res 5:81; Slob A et al., 1990. J Sex Martial Ther 16:59). Vascular risk factors of coronary diseases also increase the probability of sexual dysfunction in postmenopausal females (Sadeghi-Nejad H et al., 1996. J Urol 155:677A).

Female sexual dysfunction can be due to an impairment in endothelium dependent vasodilation and smooth muscle relaxation which in turn could lead to impairment of vascular dependent events associated with sexual functioning. During sexual arousal, an increase in vaginal blood flow occurs which in turn results in vaginal lengthening and enhanced production of vaginal fluid. Enhanced clitoral blood flow occurs during arousal leading to clitoral engorgement and erection. Impairment of these vascular dependent events can lead to impairment in vaginal lubrication and/or a diminution in vaginal enlargement during the arousal stage of female sexual function. An abnormality in these vascular dependent events could impair the arousal and/or orgasmic phases of sexual functioning.

A preclinical model of atherosclerosis in New Zealand female rabbits has demonstrated that atherosclerotic lesions reduce pelvic nerve stimulated vaginal engorgement and clitoral erection (Park K et al., 1997. Int J Impot Res 9:27). Thus, pharmacologic agents that prevent or reverse the vascular dysfunction associated with endothelial cell dysfunction, e.g., atherosclerosis might improve vaginal and clitoral responses to sexual arousal. Such therapeutical compounds could in turn lead to a decrease in sexual dysfunction associated with the arousal and orgasmic phases of sexual functioning. In addition, in females who have a coexistent reduction in desire, the alleviation of abnormalities in the arousal and orgasmic phases of sexual functioning could enhance the desire to engage in sexual activity.

SUMMARY OF INVENTION

It is an object of the invention to provide a method for inducing smooth muscle relaxation associated with sexual functioning.

It is another object of the invention to provide a method for inducing vasodilation associated with sexual functioning.

It is yet another object of the invention to provide a method for treating a sexual dysfunction in a man.

It is still another object of the invention to provide a method for treating a sexual dysfunction in a woman.

These and other objects of the invention are provided by one or more of the embodiments provided below.

In one embodiment of the invention there is provided a method for inducing smooth muscle relaxation associated with sexual functioning which comprises administering to a patient in need of such treatment a therapeutically effective amount of a particular class of protein kinase C inhibitors.

In another embodiment of the invention there is provided a method for inducing vasodilation associated with sexual functioning which comprises administering to a patient in need of such treatment a therapeutically effective amount of a particular class of protein kinase C inhibitors.

In yet another embodiment of the invention there is provided a method for treating a sexual dysfunction in a man which comprises administering to a patient in need of such treatment a therapeutically effective amount of a protein kinase C inhibitor.

In still another embodiment of the invention there is provided a method for treating a sexual dysfunction in a woman which comprises administering to a female patient in need of such treatment a therapeutically effective amount of a protein kinase C inhibitor.

The present invention identifies compounds which are effective in treating sexual dysfunction in humans.

DETAILED DESCRIPTION OF THE INVENTION

It is a discovery of the present invention that the therapeutic use of a particular class of protein kinase C inhibitors, i.e., inhibitors of the β isozyme of protein kinase C, and especially β isozyme selective inhibitors of PKC, induces vasodilation, smooth muscle relaxation, especially such events associated with sexual functioning. Consequently, such compounds can be used therapeutically to treat sexual disorders, e.g., impairment in penile erection, impotence in diabetic men and arousal and orgasm disorders in women.

The method of this invention preferably utilizes those protein kinase C inhibitors that effectively inhibit the β isozyme. One suitable group of compounds are generally described in the prior art as bis-indolylmaleimides or macrocyclic bis-indolylmaleimides. Bis-indolylmaleimides well recognized in the prior art include those compounds described in U.S. Pat. Nos. 5,621,098, 5,552,396, 5,545,636, 5,481,003, 5,491,242, and 5,057,614, all incorporated by reference herein. Macrocyclic bis-indolylmaleimides are particularly represented by the compounds of formula I. These compounds, and methods for their preparation, have been disclosed in U.S. Pat. No. 5,552,396, which is incorporated herein by reference. These compounds are administered in a therapeutically effective amount to a human to induce sexual functioning related vasodilation and smooth muscle relaxation, or to treat sexual disorders. These compounds can also be administered to patients at risk of the disease conditions mentioned above as prophylactics.

One preferred class of compounds for use in the method of the invention has the formula (I):

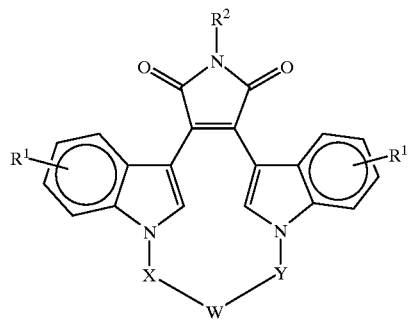

wherein:

W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form —(CH$_2$)$_n$—AA—;

R's are hydrogen or up to four optional substituents independently selected from halo, C$_1$–C$_4$ alkyl, hydroxy, C$_1$–C$_4$ alkoxy, haloalkyl, nitro, —NR$^4$R$^5$, or —NHCO(C$_1$–C$_4$ alkyl);

R$^2$ is hydrogen, CH$_3$CO—, —NH$_2$, or hydroxy;

R$^3$ is hydrogen, —(CH$_2$)$_m$aryl, —C$_1$–C$_4$ alkyl, —COO (C$_1$–C$_4$ alkyl), —CONR$^4$R$^5$, —(C=NH)NH$_2$, —SO (C$_1$–C$_4$ alkyl), —SO$_2$ (NR$^4$R$^5$), or —SO$_2$ (C$_1$–C$_4$ alkyl);

R$^4$ and R$^5$ are independently hydrogen, C$_1$–C$_4$ alkyl, phenyl, benzyl, or combine with the nitrogen to which they are bonded to form a saturated or unsaturated 5 or 6 member ring;

AA is an amino acid residue;

m is independently 0, 1, 2, or 3; and n is independently 2, 3, 4, or 5, or a pharmaceutically acceptable salt, prodrug, or ester thereof.

A more preferred class of compounds for use in this invention is represented by formula I wherein the moieties —X—W—Y— contain 4 to 8 atoms, which may be substituted or unsubstituted. Most preferably, the moieties —X—W—Y— contain 6 atoms.

Other preferred compounds for use in the method of this invention are those compounds of formula I wherein R$^1$ and R$^2$ are hydrogen; and W is a substituted alkylene, —O—, S—, —CONH—, —NHCO— or —NR$_3$—. Particularly preferred compounds for use in the invention are compounds of the formula Ia:

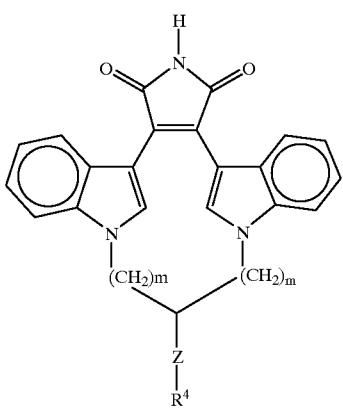

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alky; R$^6$ is hydrogen, C$_1$–C$_4$ alkyl or benzyl; p is 0, 1, or 2; and m is independently 2 or 3, or a pharmaceutically acceptable salt, prodrug or ester thereof Most preferred compounds of the formula Ia are those wherein Z is CH$_2$; and R$^4$ is —NH$_2$, —NH(CF$_3$), or —N(CH$_3$)$_2$, or a pharmaceutically acceptable salt, prodrug or ester thereof Other preferred compounds for use in the method of the present invention are compounds wherein W in formula I is —O—, Y is a substituted alkylene, and X is an alkylene. These preferred compounds are represented by formula Ib:

(Ib)

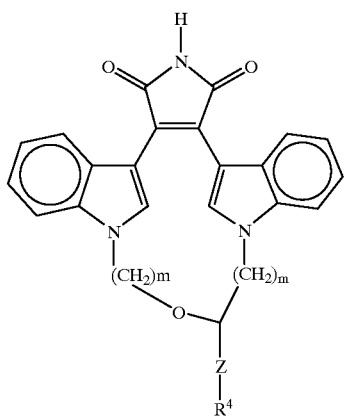

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof. Most preferred compounds of formula Ib are those wherein p is 1; and R$^5$ and R$^6$ are methyl.

Because they contain a basic moiety, the compounds of formulae I, Ia, and Ib can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4-dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and the like. Particularly the hydrochloric and mesylate salts are used.

In addition to pharmaceutically-acceptable salts, other salts also can exist. They may serve as intermediates in the purification of the compounds, in the preparation of other salts, or in the identification and characterization of the compounds or intermediates.

The pharmaceutically acceptable salts of compounds of formulae I, Ia, and Ib can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of formulae I, Ia, and Ib may exist; for example, W may contain a chiral carbon atom in the substituted alkylene moiety. The compounds are normally prepared as racemates and can conveniently be used as such. Alternatively, both individual enantiomers can be isolated or synthesized by conventional techniques if so desired. Such racemates and individual enantiomers and mixtures thereof form part of the compounds used in the methods of the present invention.

The compounds utilized in this invention also encompass the pharmaceutically acceptable prodrugs of the compounds of formulae I, Ia, and Ib. A prodrug is a drug which has been chemically modified and may be biologically inactive at its site of action, but which may be degraded or modified by one or more enzymatic or other in vivo processes to the parent bioactive form. This prodrug likely may have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H. Bundgaard, *Design of Prodrugs,* (1985).

The synthesis of various bis-indole-N-maleimide derivatives is described in Davis et aL U.S. Pat. No. 5,057,614 and the synthesis of the preferred compounds suitable for use in this invention are described in the previously identified U.S. Pat. No. 5,552,396 and in Faul et al. EP publication 0 657 411 A1, all of which are incorporated herein by reference.

One particularly preferred protein kinase-β inhibitor for use in the method of this invention is the compound described in Example 5 g ((S)-3,4-[N,N'-1,1'-((2"-ethoxy)-3'"(O)-4'"-(N,N-dimethylamino)-butane)-bis-(3,3'- indolyl)]-1(H)-pyrrole-2,5-dione Hydrochloride Salt) of the aforementioned U.S. Pat. No. 5,552,396. This compound is a potent protein kinase C inhibitor. It is selective to protein kinase C over other kinases and is highly isozyme-selective, i.e., it is selective for the beta-1 and beta-2 isozymes. Other salts of this compound also would be favored, especially the mesylate salts.

A preferred mesylate salt can be prepared by reacting a compound of the formula II:

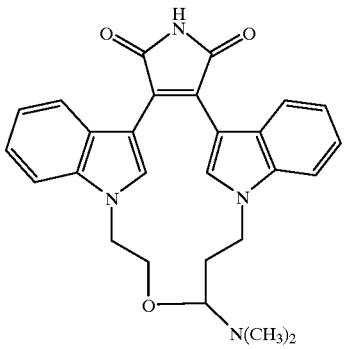

with methanesulfonic acid in a non-reactive organic solvent, preferably an organic/water mixture, and most preferably water-acetone. Other solvents such as methanol, acetone, ethylacetate and mixtures thereof are operable. The ratio of solvent to water is not critical and generally determined by the solubility of the reagents. Preferred solvent to water ratios are generally from 0.1:1 to 100:1 solvent to water by volume. Preferably, the ratio is 1:1 to 20:1 and most preferably 5:1 to 10:1. The optimal ratio is dependent on the solvent selected and is preferably acetone at a 9:1 solvent to water ratio.

The reaction usually involves approximately equimolar amounts of the two reagents, although other ratios, especially those wherein the methanesulfonic acid is in excess, are operative. The rate of addition of methanesulfonic acid is not critical to the reaction and may be added rapidly (<5 minutes) or slowly over 6 or more hours. The reaction is carried out at temperatures ranging from 0° C. to reflux. The reaction mixture is stirred until formation of the salt is complete, as determined by x-ray powder diffraction and can take from 5 minutes to 12 hours.

The salts of the present invention are preferably and readily prepared as a crystalline form. The trihydrate form of the salt may be readily converted to the monohydrate upon drying or exposure to 20–60% relative humidity. The salt is substantially crystalline demonstrating a defined melting point, birefringence, and an x-ray diffraction pattern. Generally, the crystals have less than 10% amorphous solid and preferably less than 5% and most preferably less than 1% amorphous solid.

The mesylate salt is isolated by filtration or other separation techniques appreciated in the art, directly from the reaction mixture in yields ranging from 50% to 100%. Recrystallization and other purification techniques known in the art may be used to purify the salt further if desired.

Applicants believe that endothelium is involved in the sexual functioning related to vasodilation and smooth muscle relaxation. For example, impaired endothelium dependent vasodilation seen in patients with atherosclerosis may be responsible for the vaginal dryness associated with dyspareunia and reduced clitoral erectile capacity associated with impaired orgasmic functioning. PKC inhibitors, especially PKC-β inhibitors can be used to attenuate or inhibit the endothelial cell dysfunction related to sexual functioning and therefore be therapeutically effective in inducing vasodilation and smooth muscle relaxation related to sexual functioning.

The compounds identified by the present invention can be used to treat the clinical manifestations of various sexual dysfunctions including impaired penile erection, impotence in diabetic men, arousal and orgasm disorders in women, e.g., dyspareunia and vaginismus. The compounds can also be administered as prophylaxis to people with risk factors for sexual disorders, e.g., diabetes, hypercholesterolemia, hypertension and aging.

One skilled in the art will recognize that a therapeutically effective amount of the protein kinase C inhibitor of the present invention is the amount sufficient to induce sexual functioning related vasodilation and relaxation of smooth muscle or the amount sufficient to induce penile erection, arousal, and orgasm. Such amount varies inter alia, depending upon the concentration of the compound in the therapeutic formulation, the body weight of the patient and the method of application.

Generally, an amount of protein kinase C inhibitor to be administered as a therapeutic agent will be determined on a case by case basis by the attending physician. As a guideline, the degree of impotence, the degree of impairment in arousal and organism, the duration of sexual disorder, the association with other diseases, e.g., diabetes, the body weight and the age of a patient, the mode of administration, and the like will be considered when setting an appropriate dose. Some other factors to be considered as reference are the patients hypertension, smoking habit, and overall vascular condition.

Generally, a suitable dose is one that results in a concentration of the protein kinase C inhibitor at the treatment site in the range of 0.5 nM to 200 $\mu$M, usually between 0.5 nM to 20 $\mu$M, and more usually between about 0.5 nM to 200 nM. It is expected that serum concentrations of 0.5 nM to 20 nM should be sufficient in many circumstances.

To obtain these treatment concentrations, a patient in need of treatment likely will be administered between about 0.001 mg per day per kg of body weight and 50.0 mg per day per kg. Usually, not more than about 10.0 mg per day per kg of body weight of protein kinase C inhibitor should be needed. As noted above, the above amounts may vary on a case-by-case basis.

The therapeutic effects of the methods in the present invention can be evaluated by examining the effects of the PKC isozyme selective inhibitors on endothelium-dependent vasodilation in rodent models of diabetes. Specifically, the effects of the compounds of formula I and the preferred compounds of formula Ia and Ib on acetylcholine induced vasodilation of the aorta in diabetic rats could be examined. An improvement in acetylcholine induced vasodilation in the diabetic rat is predictive of a positive response in endothelium-dependent vasodilation in female sexual functioning and of the corpus cavernosum smooth muscle in males with diabetes. The effects of the compounds on sexual functioning could also be determined by the histological appearance of the vasculature in a mouse or pig model with atherosclerosis induced by diet or diabetes. A reduction in the histologic appearance of the atherosclerotic lesion is directly related to a beneficial effect of the compounds on vasodilation and smooth muscle relaxation related to sexual functioning.

Clinical studies to test the therapeutic effects of the compounds on erectile function in impotent males with diabetes could be quanitated using nocturnal penile tumescence studies to gauge the degree and frequency of erections. In addition, the effects of the compounds on erectile function could be quantified by measuring penile tumescence while the male views an erotic video.

Clinical trials to study the therapeutic effects of the compounds on female sexual disorders can be performed via measuring vaginal blood flow during arousal. Such clinical studies can be carried out with patients of sexual disorders, diabetes, or multiple risk factors for atherosclerosis. Vaginal blood flow could be measured during sexual arousal by photophethysmography or using an oxygen-temperature electrode. An increase in blood flow during arousal would suggest an improvement in vascular and sexual functioning in these patient populations. A validated questionnaire for patients to report sexual functioning would directly measure the clinical utility of the compounds in treating and/or preventing female sexual dysfunction.

The compounds of formula I, and the preferred compounds of formula Ia and Ib are preferably formulated prior to administration. Suitable pharmaceutical formulations are prepared by known procedures using well known and readily available ingredients. In making the compositions suitable for use in the method of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders for either oral or topical application.

Some examples of suitable carriers, excipient, and diluents include lactose, dextrose, sucrose sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 0.05 mg to about 3 g, more usually about 5–15 mg of the active ingredient. However, it will be understood that the therapeutic dosage administered will be determined by the physician in the light of the relevant circumstances including the severity of the condition to be treated, the choice of compound to be administered and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, most of which may be administered orally, the compounds used in the method of the present invention also may be administered topically. Topical formulations include ointments, creams and gels. In a preferred embodiment, intracavernosal injection of the compound directly to the smooth muscle is used.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation is not critical; the concentration should be within a range sufficient to permit ready application of the formulation to the affected tissue area in an amount which will deliver the desired amount of compound to the desired treatment site.

The customary amount of a topical formulation to be applied to an affected tissue will depend upon concentration of compound in the formulation. Generally, the formulation will be applied to the effected tissue in an amount affording from about 1 to about 500 $\mu$g compound per $cm^2$ of an affected tissue. Preferably, the applied amount of compound will range from about 30 to about 300 $\mu g/cm^2$, more preferably, from about 50 to about 200 $\mu g/cm^2$, and, most preferably, from about 60 to about 100 $\mu g/cm^2$.

The following formulation examples are illustrative only and are not intended to limit the scope of the invention in any way.

Formulation 1

Hard gelatin capsules are prepared using the following ingredients:

|  | Quantity (mg/capsule) |
| --- | --- |
| Active agent | 5 |
| starch, dried | 200 |
| magnesium stearate | 10 |
| Total | 215 mg |

The above ingredients are mixed and filled into hard gelatin capsules in 460 mg quantities.

Formulation 2

A tablet is prepared using the ingredients below:

|  | Quantity (mg/capsule) |
| --- | --- |
| Active agent | 15 |
| cellulose, microcrystalline | 10 |
| silicon dioxide, fumed | 10 |
| stearic acid | 5 |
| Total | 40 mg |

The components are blended and compressed to form tablets each weighing 665 mg.

Formulation 3

Tablets each containing 60 mg of active ingredient are made as follows:

|  | Quantity (mg/tablet) |
| --- | --- |
| Active agent | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

We claim:

1. A method for inducing smooth muscle relaxation associated with sexual functioning which comprises administering to a mammal in need of such treatment, a therapeutically effective amount of an inhibitor of the β isozyme of protein kinase C.

2. The method of claim 1 wherein the inhibitor of the β isozyme of protein kinase C is a bis-indolylmaleimide or a macrocyclic bis-indolylmaleimide.

3. The method of claim 1 wherein the inhibitor is β-isozyme selective and where the isozyme selectivity is selected from the group consisting of beta-1 and beta-2 isozymes.

4. The method of claim 3 wherein the protein kinase C inhibitor has the following formula:

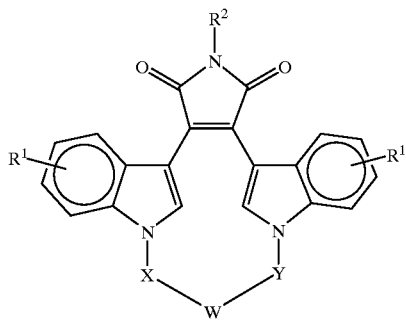

wherein:

W is —O—, —S—, —SO—, —$SO_2$—, —CO—, $C_2$–$C_6$ alkylene, substituted alkylene, $C_2$–$C_6$ alkenylene, -aryl-, -aryl($CH_2$)$_m$O—, -heterocycle-, -heterocycle-($CH_2$)$_m$O—, -fised bicyclic-, -fused bicyclic-($CH_2$)$_m$O—, —$NR^3$—, —$NOR^3$—, —CONH—, or —NHCO—;

X and Y are independently $C_1$–$C_4$ alkylene, substituted alkylene, or together X, Y, and W combine to form —($CH_2$)$_n$—AA—;

$R^1$s are hydrogen or up to four optional substituents independently selected from halo, $C_1$–$C_4$ alkyl, hydroxy, $C_1$–$C_4$ alkoxy, haloalkyl, nitro, $NR^4R^5$, or —NHCO($C_1$–$C_4$ alkyl);

$R^2$ is hydrogen, $CH_3$CO—, $NH_2$, or hydroxy;

$R^3$ is hydrogen, —($CH_2$)$_m$aryl, —$C_1$–$C_4$ alkyl, —COO ($C_1$–$C_4$ alkyl), —CONR$^4$R$^5$, —(C=NH)NH$_2$, —SO ($C_1$–$C_4$ alkyl), —$SO_2$ (NR$^4$R$^5$), or —$SO_2$($C_1$–$C_4$ alkyl);

$R^4$ and $R^5$ are independently hydrogen, $C_1$–$C_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

5. The method of claim 4 wherein the protein kinase C inhibitor has the following formula:

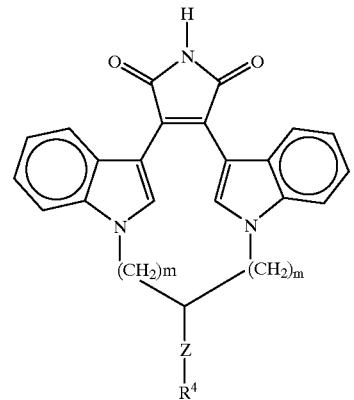

(Ia)

wherein Z is —($CH_2$)$_p$— or —($CH_2$)$_p$—O—($CH_2$)$_p$—;
$R^4$ is hydroxy, —SH, $C_1$–$C_4$ alky, ($CH_2$)$_m$aryl, —NH (aryl), —N(CH₃)(CF₃), —NH(CF₃), or —NR⁵R⁶; R⁵ is hydrogen or C₁–C₄ alky; R⁶ is hydrogen, C₁–C₄ alkyl or benzyl; p is 0, 1, or 2; and m is independently 2 or 3, or a pharmaceutically acceptable salt, prodrug or ester thereof.

6. The method of claim 4 wherein the protein kinase C inhibitor has the following formula:

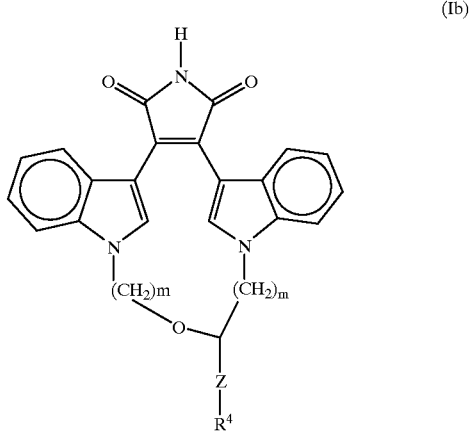

(Ib)

wherein Z is —(CH₂)_p—; R⁴ is —NR⁵R⁶, —NH(CF₃), or —N(CH₃)(CF₃); R⁵ and R⁶ are independently H or C₁–C₄ alkyl; p is 0, 1, or 2; and m is independently 2 or 3, or a pharmaceutically acceptable salt, prodrug or ester thereof.

7. The method of claim 4, wherein the protein kinase C inhibitor comprises (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione or its pharmaceutically acceptable acid salt.

8. A method of claim 7, wherein the pharmaceutically acceptable acid salt is selected from the hydrochloride salt and the mesylate salt.

9. A method for inducing vasodilation associated with sexual functioning which comprises administering to a mammal in need of such treatment, a therapeutically effective amount of an inhibitor of the β isozyme of protein kinase C.

10. A method for treating a sexual dysfunction in a male which comprises administering to a male in need of such treatment, a therapeutically effective amount of an inhibitor of the β isozyme of protein kinase C.

11. The method of claim 10 wherein the sexual dysfunction is impairment in penile erection.

12. The method of claim 10 wherein the male is diabetic.

13. A method for treating a sexual dysfunction in a female which comprises administering to a female in need of such treatment, a therapeutically effective amount of an inhibitor of the β isozyme of protein kinase C.

14. The method of claim 13 wherein the sexual dysfunction is selected from the group consisting of dyspareunia and vaginismus.

15. The method of claim 9 wherein said inhibitor is the mesylate salt of (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione.

16. The method of claim 10 wherein said inhibitor is the mesylate salt of (S)-3,4-[N,N'-1,1'-((2'"-ethoxy)-3'"(O)-4'"-(N,N-dimethylamino)-butane)-bis-(3,3'-indolyl)]-1(H)-pyrrole-2,5-dione.

17. The method of claim 12 wherein said inhibitor is the mesylate salt of (S)-3,4-[N,N'-1,1'-((2"-ethoxy)-3'"(O)-4'"-(N,N-dimethylamino)-butane)-bis-(3,3'-indoly1)]-1(H)-pyrrole-2,5-dione.

18. The method of claim 13 wherein said inhibitor is the mesylate salt of (S)-3,4-[N,N'-1,1'-((2"-ethoxy)-3 '"(O)-4'"-(N,N-dimethylamino)-butane)-bis-(3,3'-indoly1)]-1(H)-pyrrole-2,5-dione.

* * * * *